United States Patent [19]

Chang

[11] Patent Number: 4,989,592

[45] Date of Patent: Feb. 5, 1991

[54] DEVICE TO AID SEXUAL POTENCY

[76] Inventor: Dao-pin Chang, 55, Hou Hu, Hu Pei Tsun, Lin kow Hsiang, Taipei Hsien, Taiwan

[21] Appl. No.: 388,582

[22] Filed: Aug. 1, 1989

[51] Int. Cl.⁵ .............................................. A61F 5/41
[52] U.S. Cl. .............................................. 128/79
[58] Field of Search ................. 128/79, 917, 918, 158, 128/842, 844; 604/349, 347, 351, 353

[56] References Cited

U.S. PATENT DOCUMENTS 4,640,270  2/1987  Chin ........................................ 128/79
4,641,638  2/1987  Perry ....................................... 128/79

FOREIGN PATENT DOCUMENTS 2460812  7/1976  Fed. Rep. of Germany ........ 128/79

Primary Examiner—Cary E. Stone
Attorney, Agent, or Firm—Dvorak and Traub

[57] ABSTRACT

A type of device to improve male sexual potency; a penis protecting pad made of flexible material; on the upper edge of the penis protecting pad are two adjusting pads, and on its lower edges are left and right adjusting belts respectively pulled through the slots on the waist band. On the lower part of the penis protecting pad is a threaded tube joint to accommodate an inside threaded tube body. One end of the tube body is jointed and adhered to a flexible glans penis to form a penis-shaped structure to be worn onto a real penis.

7 Claims, 3 Drawing Sheets

DEVICE TO AID SEXUAL POTENCY

BACKGROUND OF THE INVENTION

The subject invention relates to a type of device to improve sexual potency, particularly to one featuring such performance as to restore male sexual power in aging and malfunctioning males, so as to provide their sexual partners with better satisfaction.

People stop getting sexual satisfaction after a period of initial relationship. Then, they experience frustrations, boredom and incompatibility. Many females would resort to masturbation to achieve climax and satisfaction. As statistics show, most females have experienced masturbation after they got married. The reason was mainly impotency in their male counterparts, who, failing to satisfy their sexual partners because of sexual malfunctioning, aging process or incompetencies, would turn to aphrodisiac drugs, herbs or food supplements, or even hypodermic injection to improve their sexual performance. Those measures would often cause adverse side effects.

In view of the above, the inventor has provided a device that could improve sexual potency to aging or incompetent males, so that they can better enjoy sexual encounters with their partners.

The subject invention is made of flexible materials, comprising of a waist band, left-right adjustable belts and a protecting pad; on an appropriate location of which is a threaded joint to mount a threaded tube. On the other end of the tube are ring grooves to match the inside threads of an immitation glans penis made of flexible material; the tube and the glans are adhered together to prevent loosening. When the subject invention is worn by an incompetent male who suffers from weak erection or premature ejaculation, it will help achieve full satisfaction to himself and his sexual partner.

SUMMARY OF THE INVENTION

The subject invention relates to a device to improve sexual potency, particularly to one made of flexible material, comprising of a band, left and right adjustable band and a penis protecting pad; on an appropriate location of the pad is a threaded joint for connection with a threaded tube to facilitate replacement, cleansing or sterilization; on the other end of the tube body can be adhered a flexible glans penis; this invention can be used to restore the sexual competency of aging or sexually incompetent males so that they can bring their sexual partners to climax and satisfaction.

BRIEF DESCRIPTION OF THE DRAWINGS

FIG. 1—1 is the wearing illustration of the penis protecting pad, left and right adjustable belts and waist band.

DETAILED DESCRIPTION OF THE PRESENT INVENTION

The subject invention relates to a device to improve sexual potency to sexually incompetent and aging males who suffer frustrations from failure to give climax or satisfaction to their sexual partners. Such sexual incompatibility could cause family dispute, family and social problems. Therefore, the subject invention has been designed to solve said problems.

Figure 1:
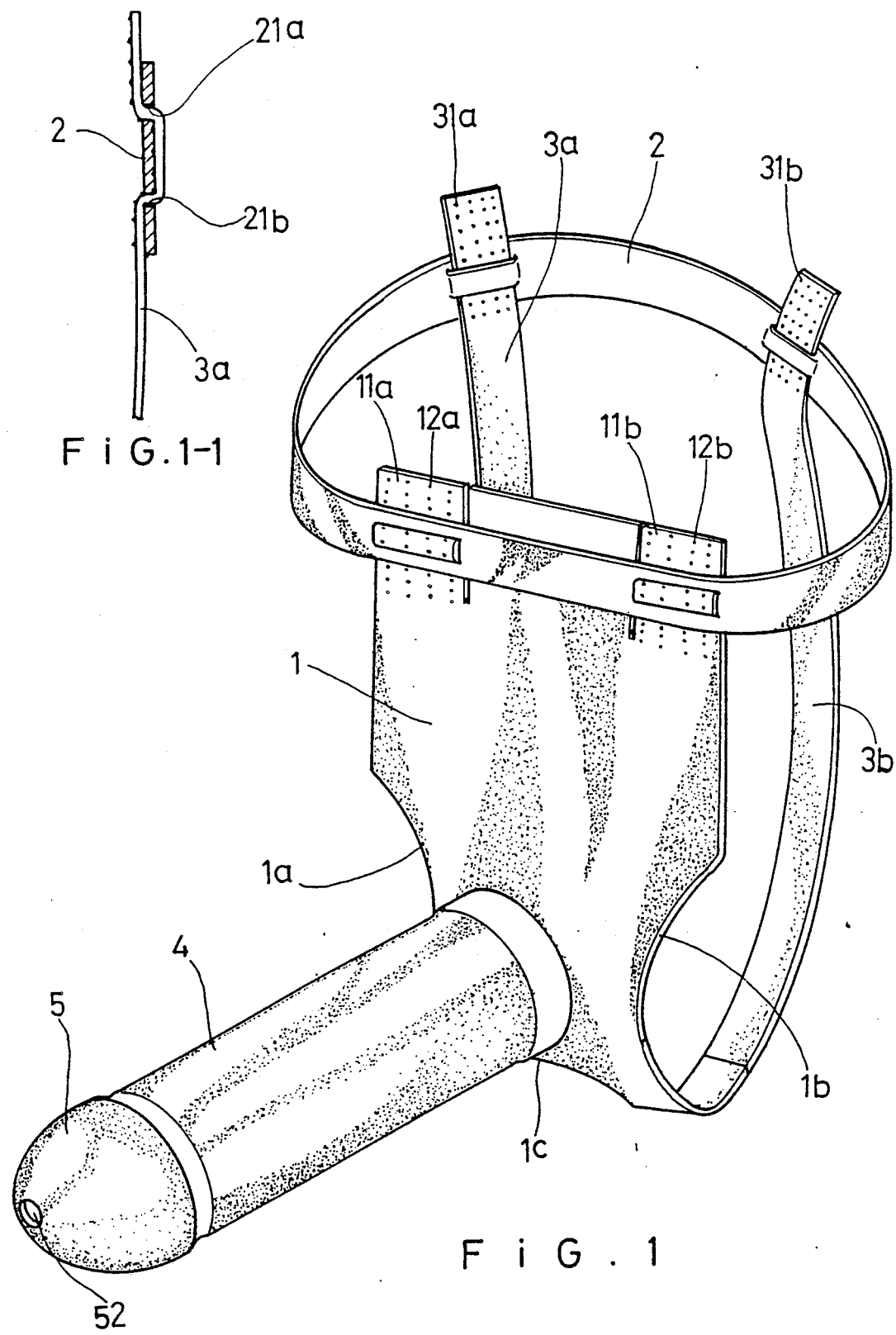
FIG. 1 is the perspective view of the invention.
Figure 2:
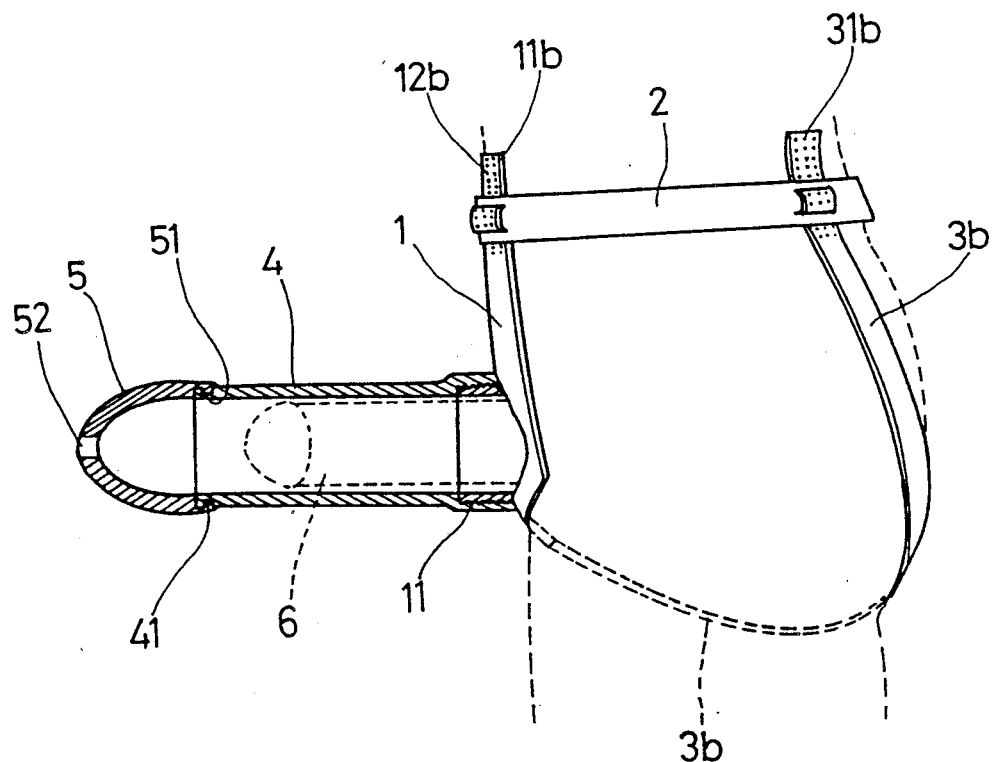
FIG. 2 is the embodiment of the invention.

Please refer to FIG. 1, 1—1 and 2 which are the perspective view and embodiment view of the penis protecting pad and left and right adjusting belts and waist band. It is clearly seen from the diagrams that at appropriate locations on the two lower sides of the waist band (2) above the penis protecting pad (1) are respectively the left and right adjusting belts (3b) (3a) which are worn inside both thighs and through the two slots (21b), (21a) on the waist band (2) to adjust the tightness (shown in FIG. 1—1). On the left and right adjusting belts (3b) (3a) are several protruding points (31b) (31a) to increase the friction and prevent loosening. On the upper edge of the protective pad (1) are pad adjustment elements 11a, 11b, having several protruding dots (12a) (12b) to increase friction effect; on the lower part of the penis protecting pad (1) is a threaded tube joint (11) with an internally threaded tube body (4). On the other end of the tube body (4) are ring grooves (41) to match the adhesion of a flexible inside-flanged (51) glans penis (5) to form a whole penis structure to solve the problems caused by male sexual incompetence. A plurality of tube bodies can be provided, the tube bodies being various sizes to accommodate different penis sizes. The two edges (1a) (1b) of the penis protecting pad (1) is curved to match human thighs curves; the lower edge (1c) of the penis protecting pad (1) is designed in arched shape to avoid pressure on the testicles.

Figure 4:
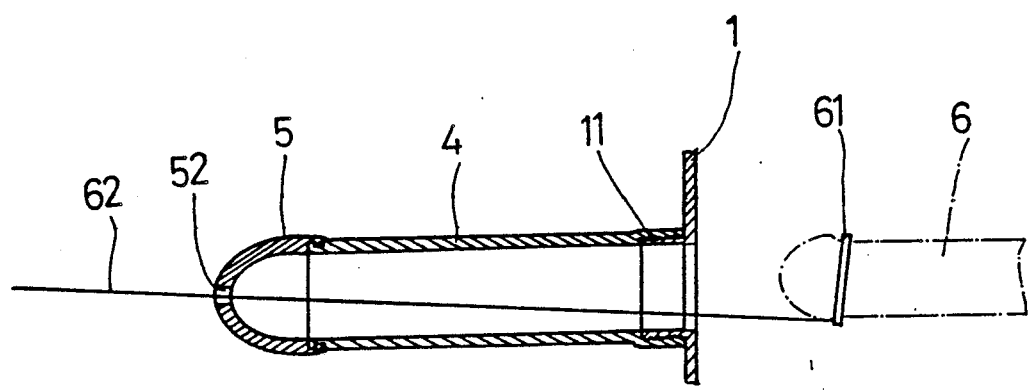
FIG. 4 is the illustration of how the invention is worn by an impotent male.
Figure 3:
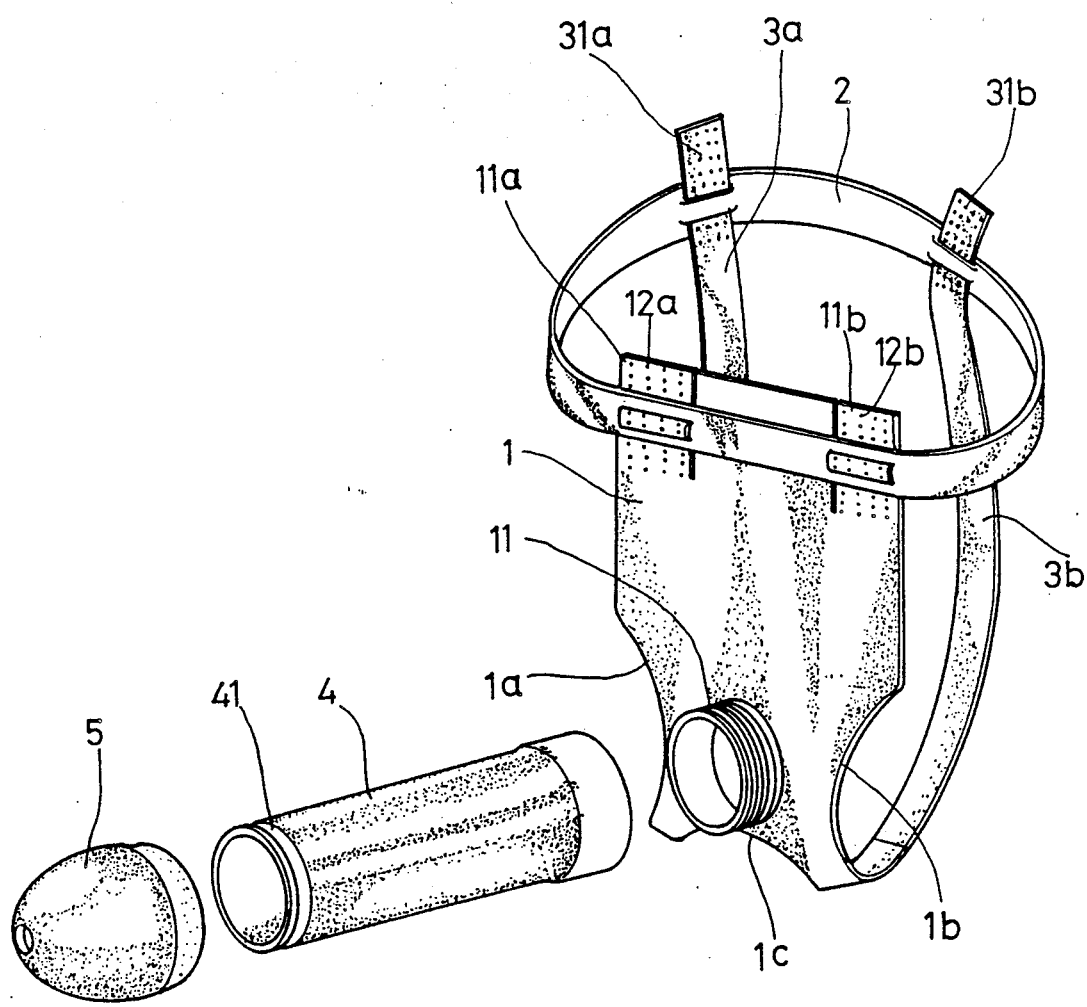
FIG. 3 is the exploded view of the invention.

As shown in FIG. 4 which illustrates the embodiment of the subject invention, on the head of a flaccid penis (6) will be mounted a rubber ring (61) which is connected with a hard cord (62) which is pulled through the hole (52) in the glans penis (5), so that the penis (5) can be pulled and worn on the invention. With a slight pull after it is worn, the rubber ring (61) will slide out of the penis (6) and be removed from the hole (52) on the glans penis (5).

I claim:

1. A device for improving male sexual potency, comprising:
   a penis protecting pad,
   arched lower edges disposed on said pad, said edges being conformed to match the shape of a human thigh,
   a tube joint disposed at a center bottom location of said pad, tube joint threads disposed on said tube joint, said tube joint forming a hole through said pad,
   a tube body, tube body threads disposed at a first end of said tube body, said tube body threads matching said tube joint threads for engagement therewith, ring grooves disposed at a second end of said tube body,
   a flexible glans penis, flanges disposed inside said glans penis, said flanges matching said ring grooves and engageable therewith, wherein said device is similar to, and may be worn on, a real penis.

2. A device for improving male sexual potency as described in claim 1, further comprising a left belt and a right belt attached to said pad, a waist band disposed at an upper edge of said pad, said waist band having belt slots which accommodate said belts, said belts being adjusted by moving said belts through said slots, thereby adjusting the tension and facilitating a better fit with respect to the thighs of the user.

3. A device for improving male sexual potency as described in claim 2, wherein said waist band is a flexible material which adjusts to accommodate various waist sizes.

4. A device for improving male sexual potency as described in claim 2, further comprising pad adjustment elements permanently attached to an upper edge of said pad, said waist band having pad adjustment slots which receive said pad adjustment elements.

5. A device for improving male sexual potency as described in claim 4, further comprising a plurality of small protuberances disposed at the ends of said pad adjustment elements, whereby said protuberances improve the adhesion between said pad adjustment elements and said pad adjustment slots.

6. A device for improving male sexual potency as described in claim 2, further comprising a plurality of small protuberances disposed at the ends of said left and said right belts, whereby said protuberances improve the adhesion between said belts and said belt slots.

7. A device for improving male sexual potency as described in claim 1, further comprising a plurality of said tube bodies, said tube bodies being sized to accommodate various penis sizes.

* * * * *